United States Patent
Patel et al.

[11] Patent Number: 6,120,664
[45] Date of Patent: Sep. 19, 2000

[54] OXYGEN ANALYZER

[76] Inventors: Nitin J. Patel; Parag N. Patel, both of P.O. Box 1226, Abingdon, Va. 24212-1226

[21] Appl. No.: 09/007,922

[22] Filed: Jan. 16, 1998

[51] Int. Cl.⁷ .................................................. G01N 27/417
[52] U.S. Cl. ........................................... 204/428; 204/424
[58] Field of Search .................................. 204/421–429; 205/782, 785

[56] References Cited

U.S. PATENT DOCUMENTS

| | | |
|---|---|---|
| 4,251,342 | 2/1981 | Habdas et al. . |
| 4,430,192 | 2/1984 | Maeda . |
| 4,462,872 | 7/1984 | Nelson . |
| 4,537,661 | 8/1985 | Lee et al. . |
| 4,784,728 | 11/1988 | Capone . |
| 4,944,861 | 7/1990 | Reber . |

*Primary Examiner*—T. Tung
*Assistant Examiner*—Jennifer McNeil

[57] ABSTRACT

An oxygen analyzer is provided including a shield probe assembly. An inner probe tube resides within the shield probe assembly. Also included is a heater assembly that is mounted to an end of the inner probe tube and situated within the shield probe assembly. A tubular sensor mechanism is removably secured within the heater assembly. A thermocouple-conductor assembly is positioned within the inner probe tube. A calibration tube has an end situated within the sensor. The thermocouple-conductor assembly and inner probe tube are conveniently accessible for repair and replacement.

2 Claims, 3 Drawing Sheets

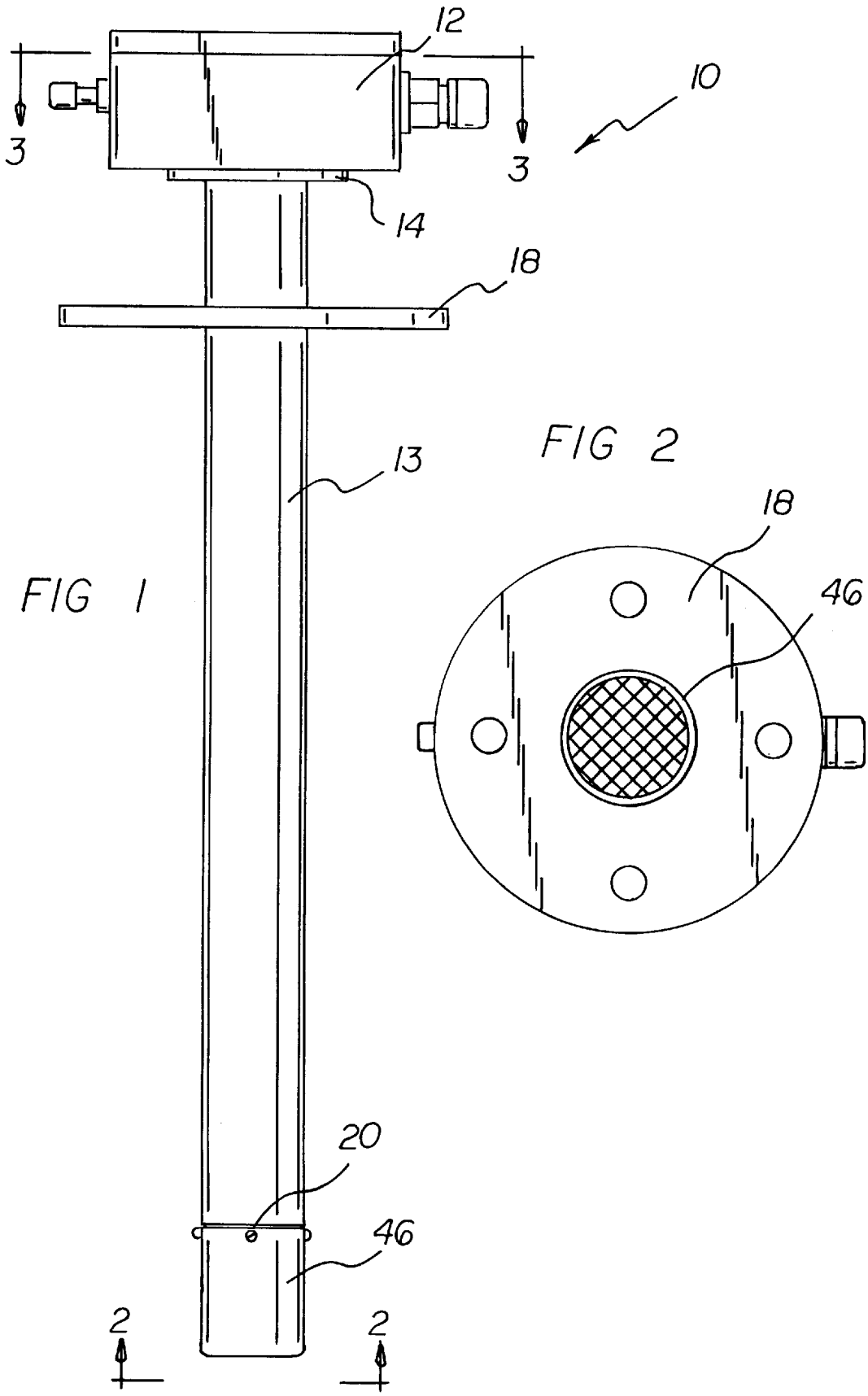

OXYGEN ANALYZER

BACKGROUND OF THE INVENTION

1. Field of the Invention

The present invention relates to an oxygen analyzer and more particularly pertains to providing an oxygen analyzer that is of a low cost, long life and further has components that may be removed for convenient replacement.

2. Description of the Prior Art

The use of oxygen analyzers is known in the prior art. More specifically, oxygen analyzers heretofore devised and utilized for various purposes are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 4,808,294; U.S. Pat. No. 5,635,044; U.S. Pat. No. 4,046,661; U.S. Pat. No. 3,616,413; U.S. Pat. No. 3,767,469; U.S. Pat. No. 3,819,500; U.S. Pat. No. 4,290,586; U.S. Pat. No. 3,454,486; U.S. Pat. No. 4,121,989; U.S. Pat. No. 3,619,381; U.S. Pat. No. 4,119,513; U.S. Pat. No. 3,940,327; U.S. Pat. No. 4,897,174; U.S. Pat. No. 5,362,344; U.S. Pat. No. 3,883,408 and U.S. Pat. No. 5,137,616.

In this respect, the oxygen analyzer according to the present invention substantially departs from the conventional concepts and designs of the prior art, and in so doing provides an apparatus primarily developed for the purpose of providing an oxygen analyzer that is of a low cost, long life and further has components that may be removed for convenient replacement.

Therefore, it can be appreciated that there exists a continuing need for a new and improved oxygen analyzer which can be used for providing an oxygen analyzer that is of a low cost, long life and further has components that may be removed for convenient replacement. In this regard, the present invention substantially fulfills this need.

SUMMARY OF THE INVENTION

In view of the foregoing known types of oxygen analyzers now present in the prior art, the present invention provides an improved oxygen analyzer. As such, the general purpose of the present invention, which will be described subsequently in greater detail, is to provide a new and improved oxygen analyzer which has all the advantages of the prior art and none of the disadvantages.

To attain this, the present invention essentially comprises a junction box preferably having a rectangular configuration, or other shape, with a front face including a circular aperture formed therein. FIG. 1 shows a rigid linear shield probe assembly having a cylindrical configuration with an open inboard end and an outboard end. The inboard end has a planar annular flange integrally coupled thereto and extending radially therefrom. The present annular flange is equipped with a first diameter and a plurality of apertures formed therein. As such, the annular flange is adapted for perpendicularly and removably coupling to the junction box. With reference still to FIG. 1, it is shown that the shield probe assembly further includes an annular planar mounting flange integrally coupled to the shield probe assembly and extended radially therefrom adjacent to and spaced from the inboard end of the shield probe assembly. The annular planar mounting flange has a diameter greater than the first diameter and a plurality of spaced apertures formed in a circular configuration. An annular recess is formed in an outer surface of the shield probe assembly at the outboard end thereof. As shown in FIG. 6, the outboard end of the shield probe assembly is closed with the exception of a central bore with a partially threaded inner periphery. Next provided is a rigid linear inner probe tube having a hollow cylindrical configuration. The inner probe tube has a second diameter that is less than the first diameter of the shield probe assembly and a length less than that of the shield probe assembly. As shown in FIGS. 4 & 5, the inner probe tube has an inboard end supported by the junction box such that the inner probe tube resides in concentric relationship with the shield probe assembly. An outboard end of the inner probe tube has a planar annular flange integrally coupled thereto. A heater assembly is provided having a hollow cylindrical configuration. An outer diameter of the heater assembly is less than the first diameter and an inner diameter of the heater assembly is no more than the second diameter. As such, a closed tubular compartment is defined for containing a heating coil therein. As shown in FIG. 6, the heater assembly has a first end connected to the planar annular flange of the inner probe tube. The heater assembly extends to the outboard end of the shield probe assembly. The heater assembly further includes a pair of bores formed in a front and a rear face thereof. During use, the heater assembly resides along an axis that is parallel with an axis about which the heater assembly is formed. Also included is a tubular sensor mechanism. By such coupling, the sensor mechanism remains within the heater assembly in coaxial alignment with the inner probe tube. A thermocouple/conductor assembly includes an elongated ceramic tube with multiple holes. The ceramic tube is situated within the inner probe tube with a plurality of supports mounted thereon. Note FIGS. 5 & 6. Each support includes a sleeve with a radial member extending therefrom for maintaining the ceramic tube along an axis of the inner probe tube. The ceramic tube has a stopper fixed adjacent to an inboard end thereof. Such inboard end is slidably situated within the circular aperture of the junction box. For urging an outboard end of the ceramic tube against the sensor mechanism, a coil spring is situated between the junction box and the stopper. Further provided is a calibration tube including an elongated linear extent situated between the inner probe tube and the shield probe assembly. This linear extent of the calibration tube is further extended through the pair of bores of the heater assembly. The calibration tube also includes a U-shaped extent situated exterior of the shield probe assembly in front of the outboard end thereof. An end of the U-shaped extent of the calibration tube extends within the second end of the sensor mechanism, as shown in FIG. 6. Finally, a filter includes a cylinder with a diameter equal to the first diameter. The filter covers an outboard end of the cylinder. A pair of threaded bores are formed on the inboard end of the cylinder for allowing it to be coupled to the outboard end of the shield probe assembly via a pair of screws.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved oxygen analyzer which has all the advantages of the prior art oxygen analyzers and none of the disadvantages.

It is another object of the present invention to provide a new and improved oxygen analyzer which may be easily and efficiently manufactured, marketed and serviced.

It is a further object of the present invention to provide a new and improved oxygen analyzer which is of a durable and reliable construction.

An even further object of the present invention is to provide a new and improved oxygen analyzer which is susceptible of a low cost of manufacture with regard to both materials and labor, and which accordingly is then susceptible of low prices of sale to the consuming public, thereby making such oxygen analyzer economically available to the buying public.

Still yet another object of the present invention is to provide a new and improved oxygen analyzer which provides in the apparatuses and methods of the prior art some of the advantages thereof, while simultaneously overcoming some of the disadvantages normally associated therewith.

Still another object of the present invention is to provide an oxygen analyzer that is of a low cost, long life and further has components that may be removed for convenient replacement.

Lastly, it is an object of the present invention to provide a new and improved oxygen analyzer including a shield probe assembly and an inner probe tube residing within the shield probe assembly. Also included is a heater assembly that is mounted to an end of the inner probe tube and situated within the shield probe assembly. A tubular sensor mechanism is removably secured within the heater assembly. A thermocouple-conductor assembly is positioned within the inner probe tube. A calibration tube has an end situated within the sensor. The thermocouple-conductor assembly, filter and inner probe tube are conveniently accessible for repair and replacement.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an illustration of the preferred embodiment of the oxygen analyzer constructed in accordance with the principles of the present invention.

FIG. 2 is a front view of the filter of the present invention.

Similar reference characters refer to similar parts throughout the several views of the drawings.

DESCRIPTION OF THE PREFERRED EMBODIMENT

Figures 3, 4:
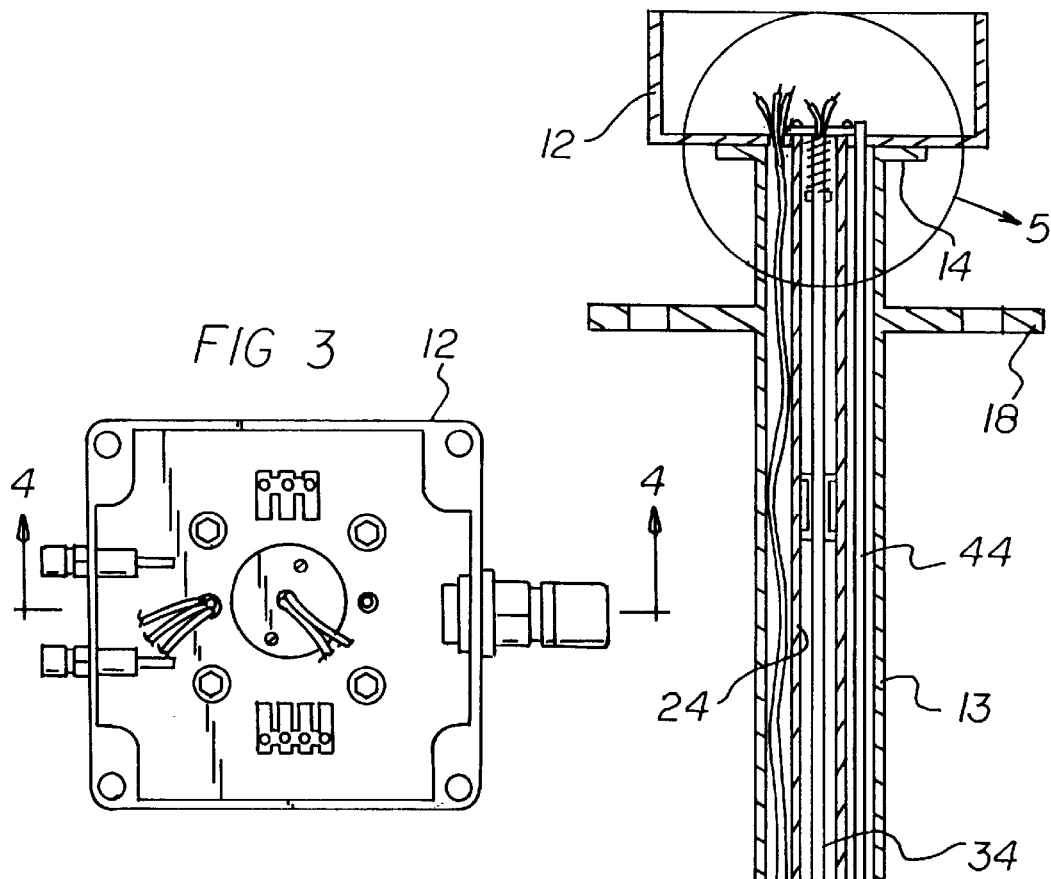
FIG. 3 is a rear view of the junction box of the present invention.
FIG. 4 is a side cross-sectional view of the present invention taken along line 4—4 shown in FIG. 3.

With reference now to the drawings, and in particular to FIG. 1 thereof, a new and improved oxygen analyzer embodying the principles and concepts of the present invention and generally designated by the reference numeral 10 will be described.

The present invention, the new and improved oxygen analyzer, is comprised of a plurality of components. Such components in their broadest context include a shield probe assembly, inner probe tube, heater assembly, sensor mechanism, calibration tube, filter, thermocouple/conductor assembly and junction box. Such components are individually configured and correlated with respect to each other so as to attain the desired objective.

More specifically, it will be noted that the system 10 of the present invention includes a junction box 12 having a rectangular configuration with a front face including a circular aperture formed therein.

FIG. 1 shows a rigid linear shield probe assembly 13 having a cylindrical configuration with an open inboard end and an outboard end. The inboard end has a planar annular flange 14 integrally coupled thereto and extending radially therefrom. The present annular flange is equipped with a first diameter and a plurality of apertures are formed therein. As such, the annular flange is adapted for perpendicularly and removably coupling to the junction box.

Figure 6:
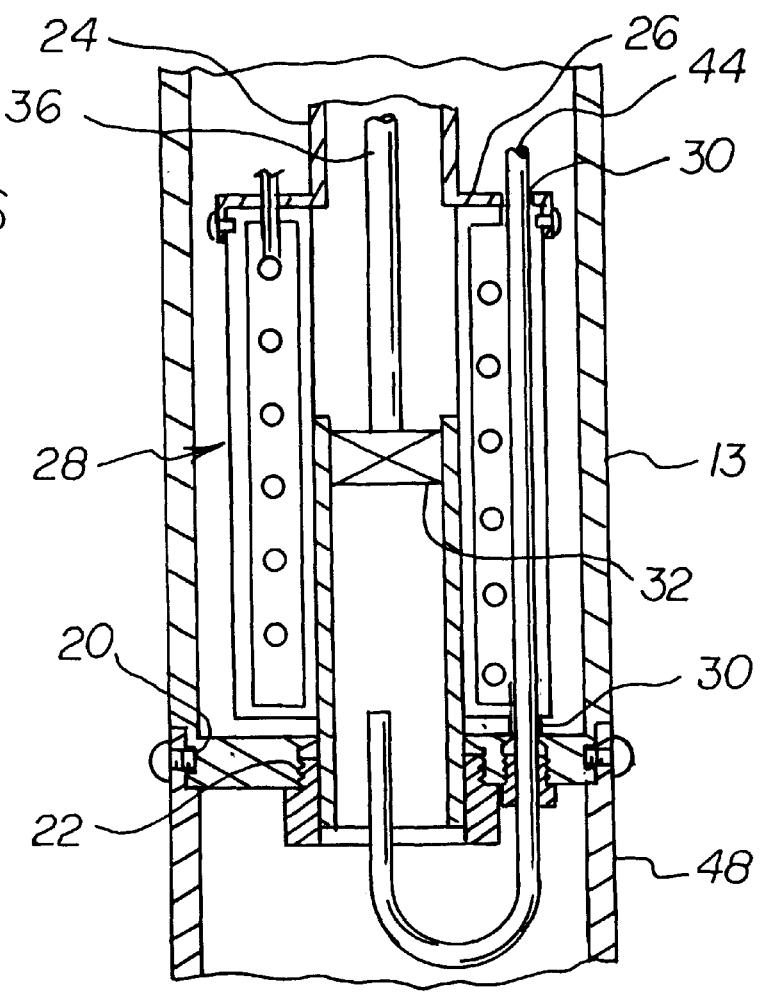
FIG. 6 is a detailed cross-sectional view of the outboard end of the present invention.

With reference still to FIG. 1, it is shown that the shield probe assembly further includes an annular planar mounting flange 18 integrally coupled to the shield probe assembly and extended radially therefrom adjacent to and spaced from the inboard end of the shield probe assembly. The annular planar mounting flange has a diameter greater than the first diameter and a plurality of spaced apertures formed in a circular configuration. An annular recess 20 is formed in an outer surface of the shield probe assembly at the outboard end. As shown in FIG. 6, the outboard end of the shield probe assembly is closed with the exception of a central bore 22 with a partially threaded inner periphery.

Figure 5:
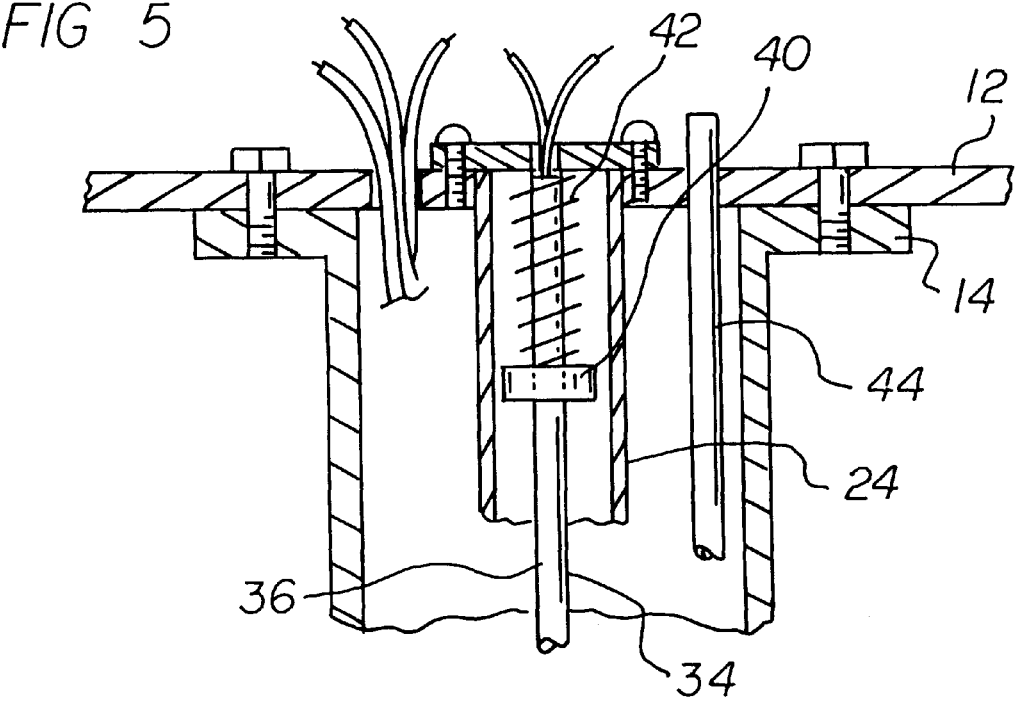
FIG. 5 is a detailed cross-sectional view of the inboard end of the present invention.

Next provided is a rigid linear inner probe tube 24 having a hollow cylindrical configuration. The inner probe tube has a second diameter that is less than the first diameter of the shield probe assembly and a length less than that of the shield probe assembly. As shown in FIGS. 4 & 5, the inner probe tube has an inboard end removably supported by the junction box such that the inner probe tube resides in concentric relationship with the shield probe assembly. Preferably, the second diameter is about ⅓ that of the first diameter such that the inner probe tube is spaced from the shield probe assembly. An outboard end of the inner probe tube has a planar annular flange 26 integrally coupled thereto. In use, the securement between the junction box and inner probe tube is such that the inner probe tube is easily removed when the junction box is disassembled.

A heater assembly 28 is provided having a hollow cylindrical configuration. An outer diameter of the heater assembly is less than the first diameter and an inner diameter of the heater assembly is no more than the second diameter. As such, a closed tubular compartment is defined for containing a heating coil therein. As shown in FIG. 6, the heater assembly has a first end screwably connected to the planar annular flange of the inner probe tube. The heater assembly extends to the outboard end of the shield probe assembly. Electrical connection of the heater coil and the junction box is afforded by way of a wire which extends through the heater assembly and the planar annular flange of the inner probe tube.

For reasons that will soon become apparent, the heater assembly further includes a pair of bores 30 formed in its front and rear face. During use, the heater assembly resides along an axis that is parallel with an axis about which the heater assembly is formed. Further, the heater assembly is spaced from the shield probe assembly.

Also included is a tubular sensor mechanism 32 having a diameter no more than the second diameter. The sensor mechanism is equipped with a first end and a second end. The second end of the sensor mechanism is coupled within the heater assembly in coaxial alignment with the inner probe tube. Preferably, the forgoing coupling is accomplished by means of a compression nut and either one or two ferrules or bushings. The compression nut and ferrules or bushings are used for not only the coupling of the sensor mechanism and shield probe assembly, but also for sealing and protection purposes. As shown in FIG. 6, the first end of the sensor mechanism is closed by a hermetically sealed sensor which ideally takes the form of a Zirconia disk sensor and thus is immune to damage resulting from thermal or mechanical shock.

A thermocouple/conductor assembly 34 includes an elongated ceramic tube 36 with multiple holes. The ceramic tube is situated within the inner probe tube with a plurality of supports mounted thereon. Note FIGS. 5 & 6. Each support includes a sleeve with at least one radial member extending therefrom for maintaining the ceramic tube along an axis of the inner probe tube. The ceramic tube has a stopper 40 fixed adjacent to an inboard end thereof. Such inboard end is slidably situated within the circular aperture of the junction box. It should be noted that the foregoing circular aperture is formed in a circular plate, or stopper washer, which is removably secured to the junction box. For urging an outboard end of the ceramic tube against the sensor mechanism, a coil spring 42 is situated between the junction box and the stopper.

Further provided is a calibration tube 44 including an elongated linear extent situated between the inner probe tube and the shield probe assembly. This linear extent of the calibration tube is further extended through the pair of bores of the heater assembly. The calibration tube also includes a U-shaped extent situated exterior of the shield probe assembly in front of the outboard end thereof. An end of the U-shaped extent of the calibration tube extends within the second end of the sensor mechanism, as shown in FIG. 6. Another end of the U-shaped extent of the calibration tube is coupled to the outboard end of the shield probe assembly by way of a hollow screw and a ferrule.

Finally, a filter 46 includes a metallic cylinder 48 with a diameter equal to the first diameter. The filter is coupled by high temperature cement to an outboard end of the cylinder. Such filter preferably takes the form of a hard abrasion resistant 5 mm thick porous non-metallic filter. A pair of threaded bores are formed on an inboard end of the cylinder for allowing it to be coupled to the outboard end of the shield probe assembly via a pair of screws.

During operation, the sensor mechanism, thermocouple/conductor assembly, heater assembly, calibration tube, and junction box function together in a conventional manner. The present invention is based on zirconium oxide sensor technology. The sensor is located at the tip of the shield probe assembly as described hereinabove. The shield probe assembly is mounted on the wall of the process in which the oxygen content of the process gases is being monitored. The present invention is designed such that when installed, the process gases and the outside atmospheric air are exposed to the opposite sides of the sensing disk in the sensor tube. The sensor mechanism senses the partial pressure of the oxygen on both sides and the pressure differential in this oxygen partial pressure causes the sensor to generate a millivolt signal proportional to this pressure differential at temperature above 650 degrees Celsius, approximately. This signal is then transmitted to the signal conditioning electronics of the junction box and used for display or control purposes.

The sensor is zirconium oxide. The zirconium oxide technology in oxygen measurement is a well-recorded prior art. The operating principle is modeled by Nerst equation:

$$EMF = KT\log(P1/P2) + C \text{(log to base 10)}$$

where,

EMF=Millivolt signal

K=Natural constant

T=Absolute Temperature(Kelvin)

P1=Partial pressure of oxygen in air

P2=Partial pressure of oxygen in process gas

C=Cell constant

In operation, the sensor is kept at a constant temperature above 650 c by the heater surrounding it. The temperature is measured by the thermocouple/conductor assembly located inside the ceramic tube assembly, and the heater is controlled electronically to maintain the desired temperature. The signal generated by the sensor is transmitted by the conductor inside the ceramic tube assembly, which maintains a positive contact by way of spring loaded ceramic tube. The power to the heater is provided from electronic package via the junction box. The junction box also facilitates the introduction of reference air during operation and introduction of calibration gas when calibration of the instrument is required. The calibration gas introduced in the junction box is carried to the process side of the sensor by the calibration tube running along the length of the shield probe and is released inside the sensor tube on the process side of the sensor. This mechanism permits calibration of the instrument on-line and while the instrument is in operation.

The filter assembly, covering the outboard tip of the shield probe assembly, contains a hard, abrasion resistant porous non-metallic material preferably five mm thick filter disk. The disk is made with controlled porosity to facilitate desired diffusion or flow of gases through the filter, and prevent dust, ash or other foreign material to enter the sensor tube and adversely effect the sensor performance.

It should be noted that the present invention has many unique features not found in the prior art including the feature whereupon either the thermocouple, conductor, ceramic tube or heater becomes non-operative or damaged, they can be replaced or repaired easily and conveniently without removing the whole instrument from the installation. The ceramic tube assembly is accessible from inside the junction box by removing the screws on the stopper washer and sliding out the ceramic tube assembly. The heater assembly can be similarly removed by removing the junction box from the inboard end of the shield probe assembly and sliding out the heater-inner tube assembly.

The replacement of the sensor does require removal of the shield probe assembly from the installation. However, the sensor can be disassembled by simply unscrewing the compression nut.

The heater cup consists of heater core on which the heating element wire is wound and the space between the core and the inner diameter of the cup is filled with insulation.

This instrument can be made in various lengths. The standard is 18 inches, 3 feet and 6 feet, or longer up to 12 feet.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An oxygen analyzer comprising:

a junction box with a front face including a circular aperture formed therein;

a rigid linear shield probe assembly having a cylindrical configuration with an open inboard end and an outboard end, the inboard end having a planar annular flange integrally coupled thereto and extending radially therefrom with a first diameter and a plurality of apertures formed therein for perpendicularly coupling to the junction box, an annular planar mounting flange integrally coupled to the shield probe assembly and extending radially therefrom adjacent to the inboard end of the shield probe assembly with a diameter greater than the first diameter wherein the annular planar mounting flange has a plurality of spaced apertures formed in a circular configuration, and an annular recess formed in an outer surface of the shield probe assembly at the outboard end thereof, wherein the outboard end of the shield probe assembly is closed with the exception of a central bore with a partially threaded inner periphery;

a rigid linear inner probe tube having a hollow cylindrical configuration with a second diameter that is less than the first diameter of the shield probe assembly and a length less than that of the shield probe assembly, the inner probe tube having an inboard end supported by the junction box such that the inner probe tube resides in concentric relationship with the shield probe assembly, an outboard end of the inner probe tube having a planar annular flange integrally coupled thereto;

a heater assembly having a hollow cylindrical configuration with an outer diameter that is less than the first diameter and an inner diameter that is no more than the second diameter such that a closed tubular compartment is defined for containing a heating coil therein, the heater assembly having a first end connected to the planar annular flange of the inner probe tube and extending to the outboard end of the shield probe assembly, the heater assembly further including a pair of bores formed in a front and a rear face thereof which reside along an axis that is parallel with an axis about which the heater assembly is formed;

a tubular sensor mechanism having a diameter no more than the second diameter, the sensor mechanism having a first end closed by a hermetically sealed sensor and a second end open to allow process gas access during operation, with a compression nut having outside male threads matably engaging the threaded inner periphery at the outboard end of the shield assembly by way of compression fittings such that the sensor mechanism remains within the heater assembly in coaxial alignment with the inner probe tube providing a gas tight seal between the inside and outside faces of the closed end of the sensor;

a thermocouple/conductor assembly including an elongated ceramic tube with multiple holes, the ceramic tube being situated within the inner probe tube, the ceramic tube having a stopper fixed adjacent to an inboard end thereof with the inboard end being slidably situated within the circular aperture of the junction box, wherein a coil spring is situated between the junction box and the stopper for urging an outboard end of the ceramic tube against the sensor mechanism;

a calibration tube including an elongated linear extent situated between the inner probe tube and the shield probe assembly and further extended through the pair of bores of the heater assembly, the calibration tube further including a U-shaped extent situated exterior of the shield probe assembly in front of the outboard end thereof, wherein an end of the U-shaped extent of the calibration tube extends within the second end of the sensor mechanism; and a filter including a cylinder with an exterior diameter equal to the first diameter with a filter covering an outboard end thereof and an inboard end thereof being equipped with internal threads formed thereon for allowing it to be coupled to external threads at the outboard end of the shield probe assembly.

2. An oxygen analyzer comprising:

a shield probe assembly having an inboard end and an outboard end with associated outwardly facing male threads;

an inner probe tube residing within the shield probe assembly;

a heater assembly removably mounted to an end of the inner probe tube and situated within the shield probe assembly;

a junction box removably supporting the inner probe tube, heater assembly, and the shield probe assembly for the repair and replacement thereof;

a sensor mechanism removably secured with respect to the heater assembly, the sensor mechanism having an inboard end located within the heater and an outboard end remote from the heater;

a filter cylinder having an inwardly threaded portion cooperable with the male threads associated with the shield probe assembly for the removable coupling therebetween to allow repair and replacement of the sensor mechanism;

a thermocouple/conductor assembly situated within the inner probe tube; and a calibration tube having an end situated within the sensor.

* * * * *